US011198742B2

(12) United States Patent
Corsa et al.

(10) Patent No.: US 11,198,742 B2
(45) Date of Patent: Dec. 14, 2021

(54) PROCESS FOR THE PURIFICATION OF HYALURONIC ACID

(71) Applicant: FIDIA FARMACEUTICI S.P.A., Abano Terme (IT)

(72) Inventors: Vincenza Corsa, Abano Terme (IT); Giancarlo Carpanese, Abano Terme (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 167 days.

(21) Appl. No.: 16/037,973

(22) Filed: Jul. 17, 2018

(65) Prior Publication Data

US 2019/0023813 A1    Jan. 24, 2019

Related U.S. Application Data

(60) Provisional application No. 62/533,798, filed on Jul. 18, 2017.

(30) Foreign Application Priority Data

Jul. 18, 2017 (IT) .................. 102017000081449

(51) Int. Cl.

| | | |
|---|---|---|
| *C08B 37/08* | (2006.01) | |
| *A61L 27/36* | (2006.01) | |
| *B01D 61/14* | (2006.01) | |
| *A61Q 19/08* | (2006.01) | |
| *A61L 27/60* | (2006.01) | |
| *A23L 33/10* | (2016.01) | |
| *A23L 33/125* | (2016.01) | |
| *A61K 8/73* | (2006.01) | |
| *A61K 9/00* | (2006.01) | |
| *A61K 31/728* | (2006.01) | |
| *A61L 15/28* | (2006.01) | |
| *A61L 15/40* | (2006.01) | |
| *A61L 15/44* | (2006.01) | |
| *A61L 27/20* | (2006.01) | |
| *A61Q 19/00* | (2006.01) | |
| *B01D 11/04* | (2006.01) | |
| *B01D 71/68* | (2006.01) | |

(52) U.S. Cl.
CPC .......... *C08B 37/0072* (2013.01); *A23L 33/10* (2016.08); *A23L 33/125* (2016.08); *A61K 8/735* (2013.01); *A61K 9/0014* (2013.01); *A61K 9/0053* (2013.01); *A61K 31/728* (2013.01); *A61L 15/28* (2013.01); *A61L 15/40* (2013.01); *A61L 15/44* (2013.01); *A61L 27/20* (2013.01); *A61L 27/3637* (2013.01); *A61L 27/3691* (2013.01); *A61L 27/60* (2013.01); *A61Q 19/00* (2013.01); *A61Q 19/08* (2013.01); *B01D 11/0492* (2013.01); *B01D 61/14* (2013.01); *B01D 61/145* (2013.01); *B01D 71/68* (2013.01); *A23V 2002/00* (2013.01); *A61K 2800/85* (2013.01); *B01D 2311/25* (2013.01); *B01D 2315/16* (2013.01); *B01D 2317/022* (2013.01)

(58) Field of Classification Search
CPC ............. C08B 37/735; C08B 37/0072; A61K 31/728; A61K 8/735; A61L 15/28; B01D 61/145; B01D 61/147; B01D 71/68
See application file for complete search history.

(56) References Cited

FOREIGN PATENT DOCUMENTS

| EP | 0716688 B1 * | 9/2003 | .............. C12P 19/26 |
|---|---|---|---|
| EP | 2870255 B1 * | 4/2016 | .............. C12R 1/46 |

OTHER PUBLICATIONS

Zhou et al., Separation of hyaluronic acid from fermentation broth by tangential flow microfiltration and ultrafiltration, Separation and Purification Technology, vol. 52, p. 29-38. (Year: 2006).*
Choi et al., Purification and biocompatibility of fermented hyaluronic acid for its applications to biomaterials, Biomaterials Research, vol. 18, p. 1-10. (Year: 2014).*
Oueslati et al., A simple methodology for predicting the performance of hyaluronic acid purification by diafiltration, Journal of Membrane Science, vol. 490, p. 152-159. (Year: 2015).*

* cited by examiner

*Primary Examiner* — Taeyoon Kim
*Assistant Examiner* — Tiffany M Gough
(74) *Attorney, Agent, or Firm* — Birch, Stewart, Kolasch & Birch, LLP

(57) ABSTRACT

A process is described for the purification of HA, and pharmaceutical, cosmetic and nutritional compositions containing HA thus purified.

5 Claims, No Drawings

PROCESS FOR THE PURIFICATION OF HYALURONIC ACID

CROSS REFERENCE TO RELATED APPLICATIONS

This non-provisional application claims the benefit under 35 U.S.C. § 119(e) to U.S. Provisional Application No. 62/533,798, filed on Jul. 18, 2017, and under 35 U.S.C. § 119(a) to Patent Application No. 102017000081449, filed in Italy on Jul. 18, 2017, all of which are hereby expressly incorporated by reference into the present application.

FIELD OF THE INVENTION

Hyaluronic acid (HA) is a high-molecular-weight polysaccharide, linear, anionic and free of sulfate groups, consisting of alternating residues of D-glucuronic acid and N-acetyl-D-glucosamine. It is present in nature in pericellular gels, in the fundamental substance of the connective tissue of vertebrate organisms (of which it represents one of the main components), in the synovial fluid of the joints, in the vitreous humor and in the umbilical cord. HA therefore plays an important role in the biological organism, above all as a mechanical support for the cells of many tissues such as skin, tendons, muscles and cartilage.

It is also known that HA, through its membrane receptors, in particular CD44, CD54 and CD168, modulates many different processes relating to the physiology and biology of the cell such as, for example, proliferation, migration, cell differentiation and angiogenesis, and that it also performs other functions such as tissue hydration and joint lubrication. It is absolutely biocompatible and, thanks to its many specific features, has been widely used for years in various fields ranging from tissue repair to viscosupplementation therapy, from dermo-aesthetic medicine to endoocular surgery, from tissue engineering to cell therapy and much more.

The chemical-physical and biological characteristics of HA are strongly correlated to its molecular weight (MW—referring to the weight average MW calculated by the "intrinsic viscosity" method), which is extremely variable: it can generally be said that the weight average MW of HA varies from 20,000 to $13 \times 10^6$ Da approximately, and the approximation is a must as it changes radically according to the source and the production and purification method used for isolating it.

There are basically two fundamental methods for obtaining HA:

production from animal sources: historically HA is extracted from animal tissues such as the umbilical cord, the vitreous humor or the bovine synovial fluid and especially rooster combs. Production from animal sources has numerous limits, it is expensive, for example, as numerous steps are required for eliminating various kinds of impurities (starting from the mass of organic residues after the digestion of the starting tissue), as steps are needed for ensuring the inactivation and elimination of any contaminating agent (such as viruses) possibly present in the starting material, it requires the availability of considerable quantities of raw material and does not give large yields;

fermentation of micro-organisms: some micro-organisms, in particular of the genus *Streptococcus* or *Pasteurella*, when appropriately stimulated and/or modified, are capable of producing HA which is secreted in the culture broth from which it is isolated through different processes, known to skilled persons in the field. Also in this case, numerous steps are required for eliminating the "impurities" present such as, for example, the residues of the cell walls of the micro-organisms used, metal ions, nucleic acids and any other undesired protein material. Despite these limitations, this is still the most developed and widely-used method for the production of HA.

New methods are also being studied for the production of HA by biotechnology, through the transfection of genes expressing the HA-synthase enzyme in suitable host cells, such as some genera of *Bacillus* (*Megaterium* and *Subtilis*) and in *Escherichia coli*. All the procedures necessary for eliminating any potentially harmful residuals are however also necessary for these production methods.

In any case, regardless of the method used, a key step in obtaining HA is obviously the extraction and purification phase of the polysaccharide. There are numerous known methods, all of which are extremely articulated and obviously modulated in relation to the starting sources for obtaining HA.

First of all, the residues of the source must be eliminated, consequently, for the extraction from animal tissue, there are digestion phases of the proteins, and subsequent filtrations, centrifugations and washings; for the fermentation, centrifugations and progressive washings are normally effected. In any case, a liquid fraction is obtained, from which the polysaccharide is then isolated. In this respect, the most widely-known and certainly the most commonly applied method, especially for HA from animal sources, is solvent precipitation: for large lines, increasing concentrations of organic solvents (ethanol, acetone) are used on the above liquid fraction, causing the hyaluronic acid to precipitate, which will then be purified by means of subsequent solubilizations and precipitations.

An alternative system involves the use of quaternary salts, for example cetyl pyridinium or cetyltrimethylammonium, with the function of complexing the polysaccharide and inducing its precipitation. Again, subsequent solubilizations and precipitations are necessary for obtaining the finished product.

The development of techniques has also combined the key steps described above in order to make the process efficient in terms of yield and effective in terms of purity: however, to date there are still many, in the order of a few hundred, adverse events reported each year to the competent bodies (for example, FDA), that have occurred especially after the injection of pharmaceutical compositions based on HA.

Hyaluronic acid is used in a wide variety of fields and pathologies: from cosmetics (for topical or oral administration) with a moisturizing action to topical dermocosmetics with a lenitive effect, from injective devices for the correction of skin defects (intradermal), whether they be wrinkles or scars, to more strictly pharmacological applications such as intra-articular use in osteoarticular pathologies, intraocularly as a substitute for the vitreous humor, intravesically for interstitial cystitis, and so forth.

Whereas for cosmetic applications, which do not touch damaged tissues, a cosmetic-grade HA (less pure) is sufficient, it is evident that in the case of pharmaceutical applications, especially injectable applications and even more so injectable in closed cavities (articulation and the eye), a degree of absolute purity is required: due to the nature of the materials from which hyaluronic acid is extracted, in fact, there may be in the finished product in residual form, nucleic acids, proteins and/or residual bacterial toxins of the cell wall of Gram-positive bacteria (for example of the genus *Bacillus*, *Streptococcus*, *Enterococcus* and *Staphylococcus*), such as lipoteicoic acid LTA or Gram-negative bacteria (such as, for example, *Escherichia Coli*, *Pasteurella* and

*Salmonella*), such as lipopolysaccharide LPS. These various kinds of contaminants are capable of causing a significant inflammatory reaction with a consequent release, at both a local and systemic level, of cytokines (particularly TNF and IL-1), in turn capable of inducing a generalized inflammatory reaction with repercussions in the whole organism, arriving, in the most serious cases, at forms of septic shock.

LTA and LPS are in fact polymers consisting of a lipid portion and a saccharide portion capable of eliciting strong immune responses and, in the most serious situations, causing arthritis, nephritis, meningitis or causing fever and shock with consequences that can also become fatal. This explains the high number of adverse events reported, as indicated above.

In addition to this, it should also be considered that, as previously mentioned, the MW of HA is variable in relation to the source and the production method, and determines its field of application: low MWs, for example, are applied in dermatological or dermocosmetic preparations (about 200 kDa, Connettivina®), whereas for intra-articular applications, higher MWs are preferred (generally ranging from 700 to 1,800 kDa; Hyalgan®, Hyalubrix®, Orthovisc®), arriving at MWs higher than 1,500 kDa used in cosmetic surgery or for intraocular applications. In the context of a purification process, however, it is essential to eliminate the fractions of HA with a MW lower than 30,000 Da, for which a strong inflammatory effect has been widely demonstrated (EP0138572), which is absolutely undesirable, regardless of the type of application.

This means that in an industrial purification process of HA, various factors must be assessed and controlled:
the process yield: it is essential to extract the maximum possible quantity of HA from the production source selected;
industrial convenience: the best product must be obtained with the minimum waste of materials used (reagents, solvents, etc.), producing the least possible quantity of residues to be disposed of and in the shortest possible time;
the degree of purity: the product obtained must be free of any contaminants and also of the fractions of HA with MW <30,000 Da, known as being able to trigger an inflammatory cascade.

The degree of purity is obviously in relation to the accuracy of the purification steps.

Numerous attempts at summarizing these requirements are known in the state of the art. Among the many, the following can be remembered, schematically:
EP0138572: purification of HA from rooster combs using, inter alia, ultrafiltration steps, the addition of quaternary salts (cetylpyridinium) and fossil resins, precipitation with ethanol and obtaining two MW fractions (50-100 kDa and 500-730 kDa), free of the inflammatory fraction; the ultrafiltrations in this context are used for eliminating all the inflammatory molecules with MW <30,000 and for separating the two desired fractions of HA;
EP535200: purification of HA from rooster combs by salifications with quaternary amines and subsequent precipitations with solvents (ethanol or acetone). HA is obtained with variable MWs ranging from 750 to 1,230 kDa, free of inflammatory fractions and specifically destined for ophthalmic use;
U.S. Pat. No. 6,489,467: purification of HA from *Streptococcus* by boost acidification with HCl, subsequent variations in pH and diafiltrations, obtaining HA with MWs of about 1,700 kDa;
Choi et al, Biomaterials Research, 2014, 18, 1-10: purification of HA from *Streptococcus zooepidemicus* by ultrafiltration and precipitation with acetone. HA is obtained with MWs ranging from 900 to 1100 kDa;
EP2870255: purification of HA from *Streptococcus zooepidemicus* by filtrations (to eliminate impurities), ultrafiltrations (to concentrate the product inside the solution in which it is present), pH variations, and finally precipitation with ethanol, obtaining an MW ranging from 60 to 2,400 kDa;
EP1543103: purification of HA from *Streptococcus* cultures by the addition of aromatic resins to the previously filtered culture broth, which adsorb most of the impurities, followed by ultrafiltration to concentrate the HA solution, and finally precipitation with ethanol.
WO2018/020458: purification of HA from cultures of micro-organisms of the genus *Streptococcus* or *Bacillus*, separated into fractions having a precise molecular weight (92-230 kDa; 450-780 kDa; 920-1450 kDa) by heat treatment. The purification includes, among other phases, steps in aromatic resins followed by repeated filtrations and finally precipitation with organic solvent and relative washings Although the processes cited herein and the processes normally used in general, are capable of producing a high-quality hyaluronic acid and with acceptable yields, they are extremely complex and therefore expensive in terms of the use of reagents, solvents, filters, etc., in terms of time and, finally, in terms of costs to be sustained for eliminating the processing residues.

The present invention overcomes the drawbacks of the known art with an extremely simplified purification process of hyaluronic acid sodium salt, which allows a very high-purity product to be obtained, together with a surprising saving of materials and time and a marked increase in the industrial yields so far known, reaching values very close to 100%.

DETAILED DESCRIPTION OF THE INVENTION

An object of the present invention relates to a new process for the extraction of hyaluronic acid and its subsequent purification in the form of an alkaline and/or alkaline-earth metal salt, preferably in the form of a sodium salt, characterized by:
a very high yield;
industrial convenience, thanks to the elimination of numerous intermediate steps;
a very high degree of purity of the final product, completely free of contaminants of any kind.

The extraction process of hyaluronic acid developed by the Applicant is extremely lean, as it provides a strictly limited number of operating steps for reaching the final product; this means a saving not only in terms of materials used (solvents, reagents, salts, fossil resins, synthetic resins, filters, etc.), but also in relation to the disposal of the processing residues: it is known that the materials used in the chemical industry must be disposed of according to safe procedures, consider the case, for example, of organic solvents. Finally, a lower number of steps also corresponds, in this case, to a reduction in the processing times; the combination of these factors leads to a better industrial convenience. This process can be applied to the purification of HA prepared according to any of the numerous techniques known to skilled persons in the field: HA can in fact derive from a biological source, in particular from avian combs of the genus *Gallus* (EP0138572), from the fermentation of *Streptococcus*, from molecular engineering from *Bacillus subtilis* and *Bacillus megaterium* (EP2614088, EP2614087); this process is preferably applicable to an HA obtained from the fermentation of *Streptococcus*, in particular *Streptococcus equi* sub-sp. *equi*, 68222, mutant H-1 (EP0716688).

The process claimed herein, as the Applicant demonstrates further on, allows the preparation of an extremely high-purity HA, not only in conformance with all the chemical/physical specifications required by the European Pharmacopoeia (Ph. Eur. 5.0 1472), but even higher, in particular in terms of the content of bacterial endotoxins, proteins, pyrogens.

It should be remembered in fact that, regardless of the production source, if the final product has not been perfectly purified, it may contain various kinds of contaminants, such as pyrogens, proteins (derived from the starting biological material), nucleic acids, toxins of a bacterial origin derived either from Gram-positive bacteria (*Streptococcus* or *Bacillus*, or from Enterococci and Staphylococci), or from Gram-negative bacteria such as, for example, *Escherichia Coli* or *Pasteurella* and *Salmonella*: the presence of these toxins, for example lipoteicoic acid (LTA) or lipopolysaccharide (LPS), in the hyaluronic acid end-product, would make it impossible to use due to the high risk of producing highly pro-inflammatory factors, in turn the cause of inflammations and/or infections of the joints or tissues treated, and in the most serious cases, causing their complete destruction or necrosis.

Finally, the yield of the purification process according to the present invention is extremely high, settling on values ranging from 85 to 100%.

The hyaluronic acid obtained according to the present invention can be used in complete safety, especially in all injective pharmaceutical compositions (intra-articular, intradermal and intraocular), as it is free of any pro-inflammatory and pyrogenic components. HA purified with the new process, object of the invention, preferably obtained in the form of an alkaline or alkaline-earth metal salt, and even more preferably in the form of sodium salt, can also be used in the preparation of all derivatives known to skilled persons in the field, such as, for example, salts of HA with heavy metals (EP0827514), esters (EP0216453), amides (EP1095064), sulfated products (EP0940410) and crosslinked products including auto-crosslinked products (EP0341745) of HA.

A further object of the invention relates to pharmaceutical, cosmetic and nutritional compositions containing HA obtained with the purification process according to the present invention, and specifically:

- pharmaceutical compositions for intra-articular use to be used in the viscosupplementation of arthritic joints, in traumatic joint damage, in subchondral damage;
- pharmaceutical compositions for intraocular use or for ocular administration for the treatment of eye diseases;
- pharmaceutical compositions to be used in the prevention of post-surgical adhesions;
- pharmaceutical compositions for topical and injective use (intradermal and/or intramuscular) in the treatment of skin ulcers, bedsores, burns of every degree, scars and skin lesions, in the treatment of keloids or hypo/hypertrophic scars, in the treatment of all types of skin defects with intact or damaged skin, and as treatment therapy for skin diseases such as eczema and various kinds of dermatitis, in particular atopic and nappy dermatitis, psoriasis;
- pharmaceutical compositions for intravesical use, in particular for the treatment of interstitial cystitis;
- pharmaceutical compositions for injective use as fillers in dermo-aesthetics or as body shaping in aesthetic surgery;
- cosmetic compositions for topical and oral use;
- pharmaceutical or nutritional compositions for the oral treatment of arthritic joints, for tendinous trophism, for cutaneous trophism and trophism of the gastro-intestinal mucous membranes.

A further object of the invention relates to two/three-dimensional biomaterials comprising the derivatives prepared with HA purified according to the invention, in the form of pads, woven fabrics, non-woven fabrics, granulates, films and gels, also possibly combined with cells of various origins and/or blood derivatives such as, for example, platelet derivatives.

As already indicated, the process according to the present invention can be applied to the purification of HA obtained according to the various known techniques as, in general, all the processes provide for some common steps, which can be summarized as follows:

Production:

depending on the source selected, the digestion of the biological material is effected, or the fermentation of appropriately identified micro-organisms or again, according to new frontiers, with biotechnological procedures. What is obtained is basically a broth heavily polluted by solid biological materials (so-called biomass), containing, in solution, hyaluronic acid and many other substances of various types, completely undesired. Each method also provides for steps for eliminating the production residues (both solid and, as far as possible, dissolved), generally by separating the biomass using various methods, so as to arrive at filtered broths containing HA, to be subjected to the subsequent extraction step:

it is in this step that the HA is isolated and recovered from the fermentation broth. This is the step in which the various known processes differ most, both in terms of operating methods (reagents, solvents, filters, surfactants, etc.), and as number of steps and therefore in terms of timing. It is certainly the most complex and delicate part of the process, as it is specifically in the extraction step that the foundations are laid for the degree of purity of the end-product and the yield of the industrial process. The result of the extraction step is in general a concentrated solution of HA which is subjected to the so-called purification step:

although the purification methods are also calibrated according to the source of origin of the hyaluronic acid, in general they follow common lines, as is known to skilled persons in the field:

the liquid phase containing hyaluronic acid in solution is treated so as to eliminate undesired elements possibly present (proteins, toxins, etc.);

precipitation is then effected with organic solvents (such as ethanol, acetone or mixtures thereof) in which HA is insoluble;

this is followed by repeated dissolutions of the precipitate in an aqueous vehicle and subsequent precipitations, solubilizations, filtrations and washings, until the final product is obtained, which is then dried.

The purification process in a broad sense (understood as a combination of steps starting from the fermentation broth leading to the final product) according to the present invention, is focused on the extraction step, which, regardless of the source of HA, in the various processes to date known, is articulated in numerous passages.

It is during this step, in fact, that the largest possible quantity of desired product (HA) must be isolated from the broth, at the same time eliminating the greatest possible quantity of all kinds of impurities, and this explains the high number of operational steps required.

It is specifically in this step, therefore, that the fundamental parameters on which a purification process is to be evaluated, are defined, i.e.:
yield, i.e. the quantity of product obtained;
purity of the product obtained;
industrial convenience, i.e. waste of materials and time for obtaining the desired product, with the desired characteristics.

The Applicant has surprisingly found that, starting from a broth coming from the production step (whatever this may be), through a reduced series of steps, the extraction process according to the present invention allows practically all the hyaluronic acid present in the broth to be extracted from the same and said HA, after appropriate purification steps according to the known art, proves to be extremely pure in terms of pyrogens, proteins, bacterial endotoxins.

An object of the present invention therefore relates to a process for the extraction and purification of HA from fermentation broth, preferably from fermentation broth of micro-organisms of the genus *Streptococcus* or *Bacillus*, in particular *S. equi, B. subtilis* or *B. megaterium*, more preferably *S. equi*, said process being characterized in that it comprises an extraction step comprising or consisting in the following steps:
a. dilution of the filtered fermentation broth with purified water, from 1.1 to 3 volumes, preferably equal to 1.5 with respect to the initial volume;
b. forced recirculation of the broth coming from step a. formed by the joining of permeate and retentate inside Tangential Flow Filter (TFF) cassettes containing ultrafiltration membranes made of arylsulfonic polymeric material, preferably polyethersulfone, with a porosity ranging from 5,000 to 300,000 Daltons, preferably from 50,000 to 200,000 and even more preferably equal to 100,000 Daltons, wherein the forced recirculation is repeated for a time ranging from 1 to 6 hours, preferably equal to 3 hours, said recirculation being conducted in a closed system, preferably with a unidirectional flow and at a constant volume without introducing liquids from the outside.

A further object of the present invention relates to an extraction process of HA from fermentation broth, preferably from fermentation broth of micro-organisms of the genus *Streptococcus* or *Bacillus*, in particular *S. equi, B. subtilis* or *B. megaterium*, more preferably *S. equi*, said process comprising or consisting in the following steps:
a. dilution of the filtered fermentation broth with purified water, from 1.1 to 3 volumes, preferably equal to 1.5 with respect to the initial volume;
b. forced recirculation of the broth coming from step a. formed by the joining of permeate and retentate inside Tangential Flow Filter (TFF) cassettes containing ultrafiltration membranes made of arylsulfonic polymeric material, preferably polyethersulfone, with a porosity ranging from 5,000 to 300,000 Daltons, preferably from 50,000 to 200,000 and even more preferably equal to 100,000 Daltons, wherein the forced recirculation is repeated for a time ranging from 1 to 6 hours, preferably equal to 3 hours, said recirculation being conducted in a closed system, preferably with a unidirectional flow and at a constant volume without introducing liquids from the outside.

The extraction process developed by the Applicant allows the almost total extraction, and therefore recovery, of the hyaluronic acid present in the initial filtered broth reaching yields ranging from 95 to 100%.

Such high extraction yields therefore result in much higher yields of finished product than what has been known so far, as, during the subsequent precipitation and washing steps typical of these processes, the only losses of HA in quantitative terms are those related to the operations (for example, minimum quantities of HA remain attached to the equipment used); it is therefore assumed that the yield of the extraction step is strongly predictive of the yield of the entire purification process.

The extraction and purification process of HA according to the present invention can provide that the forced recirculation step b. be followed by the following steps:
c. diafiltration I of the retentate contained in the TFF cassettes of step b. with a diafiltration solution selected from purified water and a saline solution, preferably purified water;
d. concentration of the volume derived from step c. up to a volume equal to that of the starting broth;
e. diafiltration II of the volume derived from step d. with a diafiltration solution selected from purified water and a saline solution, preferably purified water, repeating said diafiltration from 5 to 15 times, preferably 6-12 times;
f. final concentration of the volume derived from step e. until a final volume equal to a third of that of the starting broth is obtained;
g. recovery of the product withheld inside the TFF cassettes by the circulation of purified water until a total volume equal to half of the starting broth is obtained.

The extraction process according to the present invention has its strong point in the innovative use of the ultrafiltration technique (UF). In general, the UF technique is a known process that allows a component to be isolated from a liquid phase in which said component is contained, and having a molecular weight higher than that defined by the pores of the filtering membrane (cut-off). Very schematically, the liquid phase (feed), contained in a specific tank, is pushed by a pump against a filtering membrane provided with pores having precise dimensions (cut-off). The fluid passing through the filter membrane is collected downstream and forms the filtrate or permeate, and is disposed of; the component to be recovered is retained on the surface of the membrane and forms the retentate which contains the product of interest. In order to recover the greatest possible quantity of product, the retentate is subjected to multiple UF cycles, re-introducing it into the tank and redirecting it as feed to the UF cassettes, with elimination of the permeate obtained each time. The progressive elimination of the permeate obviously leads to a concentration due to the loss in volume, which is then compensated by adding a suitable liquid into the tank. The progressive elimination of the permeate evidently leads to a loss in hyaluronic acid, which the UF filters cannot fully retain.

In order to obtain a final product that is as pure as possible, the cycle is followed, as known to skilled persons in the field, by one or more diafiltration steps, introducing a suitable liquid (diafiltration solution) from the outside, in order to create a washing flow which, on flowing through the retentate, helps to eliminate the impurities still present. When, as in the case of the present invention, molecules of a biological origin must be separated, generally having significant dimensions in terms of Molecular Weight, the UF that is adopted is the so-called Tangential Flow Filtration (TFF).

The Applicant has therefore developed an innovative process for the extraction of HA from a fermentation broth, preferably from fermentation broth of micro-organisms of the genus *Streptococcus* or *Bacillus*, in particular *S. equi, B. subtilis* or *B. megaterium*, more preferably *S. equi*, a process which, through the innovative use of the TFF technique, allows an almost total recovery of hyaluronic acid from the broth in which it is contained.

The Applicant has in fact surprisingly found that by preceding the TFF by a dilution step and subsequent forced recirculation of the culture broth being processed, a practically total recovery of the hyaluronic acid present in the same broth is obtained. This forced recirculation is carried out, as explained in detail below, by sending the culture broth to the appropriate TFF cassettes, collecting the permeate obtained (and NOT eliminating it, as required by the state of the art) and, after conveying it inside the tank from which the original broth derives, redirecting it again to the same TFF cassettes, within which it will behave as a feed: in this way, the HA still present in the recirculating feed will constitute further retentate, and the permeate gradually produced will repeat the cycle described above (forced recirculation). In this step the retentate and permeate are therefore joined in the tank that contained the initial feed and are recirculated with a unidirectional flow. All of this takes place without introducing liquids from the outside, thus keeping the volume constant inside the system, consequently in a closed system. The whole system is naturally equipped with a series of valves that regulate the flows and outflows, variable pressure pumps for conveying the liquids, pressure gauges for the control of the pressure values.

As already mentioned above, the set of operations described determines an almost total recovery of HA from the starting broth, with yields ranging from 95 to 100%.

It is therefore evident that the invention in question substantially modifies the state of the art, significantly improving the yield of the process (more hyaluronic acid recovered) and, in cascade, the industrial convenience (fewer steps means lower quantities of materials, filters, etc . . . used and smaller quantities of waste to be disposed of).

More specifically, the operating flow through which the process described by the present invention is carried out starts, as already indicated, from a broth containing HA and coming from any initial production step, preferably from fermentation from *Streptococcus*, in particular from the fermentation of *Streptococcus equi* sub-sp. *equi*, 68222, mutant H-1 (EP0716688). In this specific case, the broth is adjusted to a pH ranging from 4.0 to 5.0, preferably 4.5 with an acid solution for strong acid, preferably HCl and subsequently separated from the biomass by means of one of the separation techniques known to skilled persons in the field (centrifugation and/or microfiltration and/or filtration on fossil flour pads).

The volume of filtered broth obviously varies according to the capacity of the industrial plant; in this specific case, the volume can vary from 2,000 liters to 4,000 liters; the method is preferably applied to a batch size of 3,000 liters. This is followed by the extraction step:
the broth thus obtained is subjected to the following steps in succession:
a. dilution: the broth coming from the production step and treated as described above, is introduced into a suitable tank and is diluted with purified water up to a total volume ranging from 1.1 to 3 volumes, preferably equal to 1.5 volumes compared to initial volume. This is a completely innovative approach, as according to the state of the art, the starting broth is concentrated, so that lower volumes must be processed;
b. forced recirculation: the broth thus diluted (feed), is circulated, by means of a system comprising a pump, inside the TFF cassettes containing UF membranes made of arylsulfonic polymeric material, preferably polyethersulfone, with a variable porosity (cut-off) ranging from 5,000 to 300,000 Daltons, preferably from 50,000 to 200,000 and even more preferably equal to 100,000 Daltons, without introducing the ultrafiltration solution and without discharging the permeate, therefore within a closed system. A forced recirculation of the broth is thus created, in which the permeate, instead of being eliminated as is normally the case, is re-introduced into the tank and joined with the retentate that is gradually produced and sent further to the filter membrane. The permeate, in fact, at least for the first cycles, contains not only mineral salts and various types of impurities, but also HA in solution. The forced recirculation of the broth also creates a gelatinous layer of HA inside the UF cassette, that acts as a further filter for the HA still present in the permeate and at the same time prevents the clogging of the system. It should be pointed out that the forced recirculation and the whole extraction system are characterized by a unidirectional flow of the liquid phase (feed and other liquids). The forced recirculation is maintained for a time ranging from 1 to 6 hours, preferably equal to 3 hours, and is tested at regular intervals of 30 minutes until a sample of permeate, brought with NaCl in powder form to a final molarity of 0.3 M in NaCl and with the addition of two volumes of ethanol, does not provide any precipitate (as already mentioned, precipitation with ethanol is one of the simplest and most immediate techniques for isolating HA from a liquid phase). This means that substantially all of the HA present in the initial broth has been retained in the TFF cassette within the retentate: it is evident that innovation virtually eliminates product losses, resulting in a huge industrial advantage.

The yield of the extraction step was calculated with the carbazole method (Ph. Eur. 5.0; 1472, January/2011); in short, the concentration of HA present in the broth at the end of the fermentation, and that of HA obtained at the end of the extraction step are determined with the carbazole method. More specifically, the ratio is calculated between the quantity in grams of HA extracted according to what is described vs the initial liters of broth at the end of the fermentation; a simple proportion allows the yield value expressed as percentage of HA extracted vs initial HA in the broth, to be calculated.

The yield of the extraction step developed within the present invention thus calculated ranges from 95 to 100%. This is followed by what is known to skilled persons in the field; in particular, the Applicant proceeds with the diafiltration steps and preferably as follows:
c. diafiltration I: the permeate derived from the previous step b., completely emptied of its HA content, is eliminated through the opening of the discharge valve. The supply of diafiltration solution is opened and is kept continuous so as to create a constant flow of diafiltration solution through the retentate, just as the volume circulating inside the tank is kept constant, through the elimination of the permeate that is gradually formed. The diafiltration solution to be used may be purified water or saline solution, preferably purified water. This procedure is maintained for the time necessary for eliminating a volume of permeate equal to twice that present in the tank at the end of the forced recirculation step.
d. concentration: keeping the discharge open and blocking the supply of diafiltration solution, the content of the tank is concentrated until it is brought back to the volumes of the starting broth before the initial dilution (therefore before step a.).
e. diafiltration II: the diafiltration step is repeated on the volume derived from step d., as described in step c. for 5-15 times, preferably 6-12 times.

Finally, the recovery of HA is effected, according to the known art, and preferably through final concentration: the same procedure is adopted as described in item d., until a final volume equal to about a third of the initial volume (before step a.) is obtained, and subsequent recovery:
the product retained inside the cassettes is recovered by the circulation of purified water until a volume equal to half of the volume of the broth before the initial dilution (therefore before step a.) is obtained.

At this point, the HA present in the solution obtained from the process described above passes to the specific purification step, which is appropriately selected by the skilled person in the field, as it is a known technique, and to the subsequent drying step.

In short, the object of the present invention relates to a highly efficient procedure for the extraction of HA in terms of yield, product purity and industrial convenience, when applied within an overall extraction and purification process of HA produced by fermentation from micro-organisms of the genus *Streptococcus* or *Bacillus*, in particular *S. equi*.

Its totally innovative feature lies in the fact that the TFF is preceded by a dilution step and forced recirculation of the culture broth being processed; this procedure can be successfully applied within any known global process for the production and purification of HA, regardless of the source of HA, the way in which this source is treated and the manner in which it reaches the final product in dried form, ready for the use for which it is destined.

More specifically, the Applicant is claiming a procedure for the extraction of HA with a high yield starting from a broth obtained according to the known techniques, in particular obtained by fermentation from *Streptococcus*, more preferably by the fermentation of *Streptococcus equi* sub-sp. *equi*, 68222, mutant H-1 (EP0716688), comprising or consisting in the following steps:

Extraction:
a. dilution: the filtered production broth is diluted with purified water up to a volume ranging from 1.1 to 3 volumes, preferably equal to 1.5 with respect to the initial volume;
b. forced recirculation: the broth coming from step a. formed by the joining of retentate and permeate, is subjected to forced recirculation inside Tangential Flow Filter (TFF) cassettes containing ultrafiltration membranes made of arylsulfonic polymeric material, preferably polyethersulfone, with a porosity ranging from 5,000 to 300,000 Daltons, preferably from 50,000 to 200,000 and even more preferably equal to 100,000 Daltons. The forced recirculation is repeated for a time ranging from 1 to 6 hours, preferably equal to 3 hours, until the complete retention of HA inside the retentate, said recirculation being carried out in a closed system, preferably with a unidirectional flow and at a constant volume without the introduction of liquids from the outside.

The procedure according to what is known to skilled persons in the field is then adopted, in particular with the diafiltration steps and preferably as follows
c. diafiltration I: this is carried out with a diafiltration solution selected from purified water and saline solution, preferably purified water, and is maintained for the time necessary for eliminating a volume of permeate equal to twice that present in the tank after the previous step b.;
d. concentration: the contents of the tank are concentrated up to the volume of the starting broth (before step a.);
e. diafiltration II: a diafiltration according to what is described in step c. is repeated for 5-15 times, preferably 6-12 times, on the volume derived from step d.;
f. final concentration: the volume derived from step e. is concentrated until a volume equal to a third of the initial volume (before step a.) is obtained;
g. recovery: the product retained inside the cassettes is recovered by the circulation of purified water until a total volume equal to half of the broth before step a. is obtained.

Once all the steps described herein have been completed, the so-called purification steps are carried out using the techniques known to those skilled in the art; only by way of example, treatment with strong alkaline or alkaline-earth bases, preferably alkaline and in particular NaOH, can be mentioned, in order to eliminate any further possible pollutants, followed by filtrations (for example, on coal and/or on filtering cloths and/or on polypropylene), precipitations in organic solvents, such as, for example, ethanol, with varying dilutions and finally washings in organic solvents, (preferably ethanol); among the various purification processes, that described in Example 3 of WO2018/020458, an integral part of the present description, is particularly preferred.

Regardless of the purification process selected, salified HA is obtained, preferably in the form of sodium salt.

The salified HA thus purified is then subjected to drying which allows its optimum preservation before being adopted for the uses for which it is destined.

The product thus obtained proves not only to comply with the parameters of the European Pharmacopoeia (Ph. Eur. 5.0; 1472), but to be even higher in terms of content of bacterial endotoxins and proteins.

The final process yield, calculated using the carbazole method (Ph. Eur. 5.0; 1472) previously described, confirms that the loss of product is minimum in this phase and due to the operational limits; the yield in fact settles within a range of 85 to 100%, preferably ranging from 95 to 100%.

Example 1: Extraction of HA from Fermentation Broth of *Streptococcus equi*

3,000 liters of fermentation broth of *Streptococcus equi* sub-sp. *equi*, 68222, mutant H-1 are brought to pH=4.5 by the addition of a 1N HCl solution under stirring and subsequently deprived of the biomass by filtration with Celite pads (diatomaceous fossil flour).

The broth thus treated is then diluted with 1,500 liters of purified water, up to a final volume of 4,500 liters, and placed in a reactor having a suitable capacity (6,000 liters).

The volume of broth obtained is subjected to the forced recirculation step, using TFF cassettes (Pall, Omega model), provided with polyethersulfone membranes with a porosity (cut-off) equal to 100,000 Daltons. The feed is introduced into the cassettes with an inlet pressure not higher than 2.5 bars, exerted by the pump. The forced recirculation is maintained for 3 hours and, at 30 minute intervals, an assay is effected to evaluate the presence of HA in the permeate: 32 ml of NaCl and two volumes of ethanol are added to 2 ml of permeate. At the end of the 3 hours of forced recirculation, the test gives a negative result, i.e. no precipitate is formed, meaning that the HA has been entirely retained in the retentate.

The forced recirculation is blocked and the yield is calculated with the carbazole method described above, which is equal to 98%. The first diafiltration step is then started at a constant volume, by the introduction of purified water into the collection tank, for the time necessary for passing, through the UF cassettes, a quantity of water equal to 9,000 liters, therefore equal to twice the volume present in the tank. In this step, the discharge valve is opened and 9,000 liters of permeate, directed towards a specific disposal container, are eliminated.

The volume of retentate is now concentrated to the starting volume (3,000 liters), by closing the supply of purified water whereas the discharge remains open.

The diafiltration is repeated with purified water until the elimination of a total of 24,000 liters of permeate, thus completing 8 diafiltration cycles.

The final concentration of the solution is then effected by closing the supply of purified water, up to a volume of 1,000 liters. The product is then recovered with purified water: keeping the discharge valve closed, 500 liters of water are added to the tank, in successive fractions. The water is circulated inside the system, continuously recovering the retentate and re-introducing it into the feed, in order to detach all of the HA contained in the TFF cassettes and that adhering to the walls of the system; a final volume of 1,500 liters is thus obtained, which is optimum for the subsequent purification steps, said purification being carried out according to what is described in Example 3 of WO2018/020458 until the final product, hyaluronic acid in the form of sodium salt, is obtained in dried powder.

More specifically, 0.2 M NaOH in water is added to the product recovered and the whole mixture is then neutralized with 12N HCl until the pH is brought to 8.5 and finally filtered through a polypropylene filter. The HA solution, now in the form of a sodium salt, is precipitated with absolute ethanol and kept under stirring for 30 minutes. The product is left to settle for 10 minutes and the supernatant is eliminated by siphoning. The product is washed with a mixture of ethanol:water (80:20) under continuous stirring for 30 minutes, and the supernatant is then eliminated by siphoning. The last washing is effected with absolute ethanol which is finally eliminated by filtration. The product obtained is placed in special stainless steel trays and dried for at least 22 hours at a temperature of 25° C. under vacuum.

Analysis of the Final Product:
protein content: <0.1%, compliant with Ph. Eur. 5.0, 1472
content of bacterial endotoxins: <0.05%, compliant with Ph. Eur. 5.0, 1472
yield: 96.2%

The data presented herein clearly show that the insertion of the extraction process, object of the present invention, within a process for the production, extraction and purification of hyaluronic acid by fermentation of micro-organisms known in the state of the art, surprisingly increases the process yield in its entirety, allowing a much greater improvement in its efficiency than what is so far known in the state of the art.

In this respect, it should be remembered that in general the yield of known processes considered particularly efficient is established between 60 and 80%.

The insertion of the extraction step or process developed by the Applicant also makes the overall process industrially more convenient; steps for the addition of complexing salts or adsorbent resins, filtrations on cloths or filters, repeated solubilization and precipitation phases with organic solvents are in fact eliminated, thus leading to a net saving both in terms of processing times and the use of materials and finally also in terms of waste to be disposed of

The invention claimed is:

1. A process for the extraction and purification of hyaluronic acid (HA) from fermentation broth of micro-organisms of the genus *Streptococcus* or *Bacillus* which consists of:

a. dilution of filtered fermentation broth with purified water, from 1.1 to 3 volumes with respect to the initial volume;

b. forced recirculation of the broth coming from step a. formed by joining of retentate and permeate inside Tangential Flow Filter (TFF) cassettes containing ultra-filtration membranes made of arylsulfonic polymeric material with a molecular weight cut-off ranging from 5,000 to 300,000 Daltons, wherein the forced recirculation is repeated for a time ranging from 1 to 6 hours, said recirculation being conducted with a unidirectional flow and in a closed system, at a constant volume without introducing liquids from the outside;

wherein the process yield of steps a. and b. ranges from 95 to 100% of the hyaluronic acid present in the filtered fermentation broth, and wherein the forced recirculation step b. is followed by the following steps:

c. diafiltration I of the retentate contained in the TFF cassettes of step b. with a diafiltration solution selected from purified water and a saline solution;

d. concentration of the volume derived from step c. up to a volume equal to that of the initial volume;

e. diafiltration II of the volume derived from step d. with a diafiltration solution selected from purified water and a saline solution, repeating said diafiltration from 5 to 15 times;

f. final concentration of the volume derived from step e. until a final volume equal to a third of that of the initial volume is obtained;

g. recovery of the product retained inside the TFF cassettes by the circulation of purified water until a total volume equal to half of the initial volume is obtained.

2. A process for the extraction and purification of hyaluronic acid (HA) from fermentation broth of micro-organisms of the genus *Streptococcus* or *Bacillus* which consists of:

a. dilution of filtered fermentation broth with purified water, from 1.1 to 3 volumes with respect to the initial volume;

b. forced recirculation of the broth coming from step a. formed by joining of retentate and permeate inside Tangential Flow Filter (TFF) cassettes containing ultra-filtration membranes made of arylsulfonic polymeric material with a molecular weight cut-off ranging from 5,000 to 300,000 Daltons, wherein the forced recirculation is repeated for a time ranging from 1 to 6 hours, said recirculation being conducted with a unidirectional flow and in a closed system, at a constant volume without introducing liquids from the outside;

wherein the process yield of steps a. and b. ranges from 95 to 100% of the hyaluronic acid present in the filtered fermentation broth, and wherein the forced recirculation step b. is followed by the following steps:

c. diafiltration I of the retentate contained in the TFF cassettes of step b. with a diafiltration solution selected from purified water and a saline solution;

d. concentration of the volume derived from step c. up to a volume equal to that of the initial volume;

e. diafiltration II of the volume derived from step d. with a diafiltration solution selected from purified water and a saline solution, repeating said diafiltration from 5 to 15 times;

f. final concentration of the volume derived from step e. until a final volume equal to a third of that of the initial volume is obtained;

g. recovery of the product retained inside the TFF cassettes by the circulation of purified water until a total volume equal to half of the initial volume is obtained; and h. further purifying the product obtained in step g., wherein the purified HA has a total protein content <0.1% and a content of bacterial endotoxins <0.05%.

3. The process according to claim 1, wherein the fermentation broth is a fermentation broth of *Streptococcus equi* sub-sp. *equi* 68222, mutant H-1.

4. The process according to claim 2, wherein the purified HA is in the form of a salt of alkaline or alkaline-earth metals.

5. The process according to claim 1, wherein the ultrafiltration membranes are made of polyethersulfone.

* * * * *